(12) United States Patent
Yang et al.

(10) Patent No.: US 11,357,823 B2
(45) Date of Patent: Jun. 14, 2022

(54) METHOD FOR TREATING CEREBRAL STROKE

(71) Applicant: Suzhou Yabao Pharmaceutical R&D Co., Ltd., Jiangsu (CN)

(72) Inventors: Lei Yang, Jiangsu (CN); Guoning Lian, Jiangsu (CN); Xiaoping Gao, Jiangsu (CN); Lin Zhu, Jiangsu (CN)

(73) Assignee: SUZHOU YABAO PHARMACEUTICAL R&D CO., LTD, Jiangsu (CN)

( * ) Notice: Subject to any disclaimer, the term of this patent is extended or adjusted under 35 U.S.C. 154(b) by 0 days.

(21) Appl. No.: 16/742,131

(22) Filed: Jan. 14, 2020

(65) Prior Publication Data
US 2021/0060122 A1   Mar. 4, 2021

(30) Foreign Application Priority Data

Aug. 30, 2019   (CN) .......................... 201910815496.0

(51) Int. Cl.
| | |
|---|---|
| *A61K 38/00* | (2006.01) |
| *A61K 38/17* | (2006.01) |
| *A61P 25/00* | (2006.01) |
| *A61K 9/00* | (2006.01) |
| *A61K 45/06* | (2006.01) |

(52) U.S. Cl.
CPC ........ *A61K 38/1709* (2013.01); *A61K 9/0019* (2013.01); *A61P 25/00* (2018.01); *A61K 45/06* (2013.01)

(58) Field of Classification Search
CPC .. A61K 38/1709; A61K 9/0019; A61K 45/06; A61P 25/00
See application file for complete search history.

(56) References Cited

U.S. PATENT DOCUMENTS

| | | | | |
|---|---|---|---|---|
| 9,192,649 | B2 * | 11/2015 | Feng ...................... | A61P 29/00 |
| 2009/0291086 | A1 * | 11/2009 | Allison .............. | A61K 38/1709 424/141.1 |
| 2017/0239329 | A1 * | 8/2017 | Frosteg Rd et al. ......................... | A61K 38/1709 |

FOREIGN PATENT DOCUMENTS

| | | | |
|---|---|---|---|
| WO | WO-2012136819 A1 * | 10/2012 | ........... A61K 31/616 |

OTHER PUBLICATIONS

Iadecola et al. 2012. The immunology of stroke: from mechanisms to translation. Nat Med. ; 17(7): 796-808. (Year: 2012).*
Okada et al. The Stroke-Induced Blood-Brain Barrier Disruption: Current Progress of Inspection Technique, Mechanism, and Therapeutic Target. Current Neuropharmacology 18: 2020 (Year: 2020).*
Chen Bo. Role of blood-brain barrier leakage during stroke. UC San Diego Electronic Theses and Dissertations (Year: 2010).*
Abdullahi et al. Blood-brain barrier dysfunction in ischemic stroke: targeting tight junctions and transporters for vascular protection. Am J Physiol Cell Physiol . Sep. 1, 2018;315(3):C343-C356. (Year: 2018).*
Lorberboym et al. Brain Research vol. 1103, Issue 1, Aug. 4, 2006, pp. 13-19. In vivo imaging of apoptosis in patients with acute stroke: Correlation with blood-brain barrier permeability. (Year: 2006).*
Bederson J. et al., "Evaluation of 2,3,5-triphenyltetrazolium chloride as a stain for detection and quantification of experimental cerebral infarction in rats", Stroke vol. 17, No. 6, Nov. 1986, p. 1304-1308.
Bederson J. et al., "Rat middle cerebral artery occlusion: evaluation of the model and development of a neurologic examination", Stroke, vol. 17, No. 3, May 1986, p. 472-476.
Huber R. et al., "Crystal and molecular structure of human annexin V after refinement. Implications for structure, membrane binding and ion channel formation of the annexin family of proteins", Journal of Molecular Biology, vol. 223, Issue 3, Feb. 1992, p. 683-704.
Jolkkonen J. et al., "Behavioral deficits and recovery following transient focal cerebral ischemia in rats glutamatergic and GABAergic receptor densities", Behavioural Brain Research vol. 138, Issue 2, Jan. 2003, p. 187-200.
Longa E. Z. et al., "Reversible middle cerebral artery occlusion without craniectomy in rats", Stroke vol. 20, No. 1, Jan. 1989, p. 84-91.
Yang Y. et al, "Quantification of infarct size on focal cerebral ischemia model of rats using a simple and economical method", Journal of Neuroscience Methods, vol. 84, Issue 1-2, 1998, p. 9-16.

* cited by examiner

*Primary Examiner* — Aradhana Sasan
*Assistant Examiner* — Mercy H Sabila
(74) *Attorney, Agent, or Firm* — Fox Rothschild LLP

(57) ABSTRACT

The invention relates to the field of biomedicine, in particular to the use of annexin A5 in the treatment of cerebral stroke. The invention provides a method for treating cerebral stroke and a drug combination containing annexin A5. The method can reduce cerebral infarction, improve symptoms of neurobehavioral deficits in the brain and treating stroke.

6 Claims, 1 Drawing Sheet

Specification includes a Sequence Listing.

SEQUENCE LISTING

```
<160> NUMBER OF SEQ ID NOS: 1

<210> SEQ ID NO 1
<211> LENGTH: 319
<212> TYPE: PRT
<213> ORGANISM: Artificial Sequence
<220> FEATURE:
<223> OTHER INFORMATION: Annexin A5

<400> SEQUENCE: 1

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
```

```
                    180                 185                 190
Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
        210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
                260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
        290                 295                 300

Gly Asp Tyr Lys Lys Ala Leu Leu Leu Leu Cys Gly Glu Asp Asp
305                 310                 315
```

METHOD FOR TREATING CEREBRAL STROKE

RELATED APPLICATIONS

This application claims priority and benefits of Chinese Patent Application No. 201910815496.0, filed with State Intellectual Property Office on Aug. 30, 2019, the entire content of which is incorporated herein by reference.

FIELD

The invention relates to the field of biomedicine, in particular to the method for treating cerebral stroke.

BACKGROUND

"Cerebral stroke" is also known as "stroke" or "cerebrovascular accident" (CVA). It is an acute cerebrovascular disease. It is a group of diseases, including ischemic and hemorrhagic stroke, caused by sudden rupture of blood vessels in the brain or the failure of blood to flow into the brain due to blockage of blood vessels. The incidence of ischemic stroke is higher than that of hemorrhagic stroke, accounting for 60%-70% of the total number of stroke. Clinical studies have shown that many factors can induce stroke.

Stroke is characterized by high morbidity, disability, recurrence and mortality. Drug therapy for stroke needs further improvement.

SUMMARY

One object of the present invention is to provide a method for treating cerebral stroke.

Annexin belongs to calcium-dependent phospholipid binding protein family, which is widely expressed and has many important functions. Some annexins, such as annexin A1, are closely related to tumors and are highly expressed in pancreatic cancer, liver cancer and head and neck tumors. Some annexins, such as Annexin A5 (or A5), have anti-inflammatory and anticoagulant functions.

Annexin A5 is a calcium-dependent channel protein that binds to the surface of negatively charged phospholipids. Its molecular weight is about 34 kDa. It mainly exists in the cell membrane and endoplasmic reticulum. Its high molecular weight usually prevents it from entering brain tissue. Therefore, little research has been done in the nervous system. The present inventors noticed that in the case of acute injury (stroke, etc.), the blood-brain barrier is destroyed and A5 enters the brain. Radioactive labeled A5 protein was distributed in the brain as a developer. In addition, annexin A5 has the functions of anti-inflammation, anti-coagulation, improving endothelial injury and organ dysfunction. The annexin A5 entering the brain can be used to treat brain diseases and repair brain nerve injury, such as cerebral ischemia-reperfusion injury, so as to treat stroke diseases.

Annexin A5 may be, but not limited to, a full-length natural human Annexin A5 polypeptide or its variant. A5 polypeptides can be provided from any source or method, such as natural isolates or recombinant or synthetic sources or appropriate combinations of above. The polypeptide sequence of annexin A5 can be based on complete or partial natural amino acid sequences or on variants of these complete or partial natural amino acid sequences.

Particularly, the invention provides the following technical solution:

In one aspect of present disclosure, a method for treating cerebral stroke is provided, and according to embodiments of present disclosure, the method comprise: administrating an annexin A5 or a functional equivalent thereof to a patient in need of such treatment or administrating an effective dose annexin A5 or a functional equivalent thereof to a patient in need of such treatment. In this article, "effective dose" or "therapeutic effective dose" refers to the dosage of drugs that can exert the therapeutic functions of stroke mitigation or rehabilitation. Inventors have found that annexin A5 can be used to treat stroke, which can be used to prepare drugs for stroke, and there is no risk of bleeding during treatment. In the course of treatment, it can repair part of the blood-brain barrier and repair nerve damage in the brain.

According to the embodiment of the present invention, the method for treating cerebral stroke as described above may further include the following technical features:

According to embodiments of present disclosure, the functional equivalent have at least 80% identity with SEQ ID NO:1.

According to embodiments of present disclosure, the functional equivalent have at least 90% identity with SEQ ID NO:1.

According to embodiments of present disclosure, the functional equivalent have at least 95% identity with SEQ ID NO:1.

According to embodiments of present disclosure, the functional equivalent have at least 99% identity with SEQ ID NO:1.

According to embodiments of present disclosure, the cerebral stroke is ischemic stroke. Annexin A5 can improve neurobehavioral deficits caused by ischemic stroke, such as limb paralysis, reduce the area of cerebral infarction, so as to achieve the goal of treating ischemic stroke.

According to embodiments of present disclosure, the cerebral stroke involves overactivation of immune cells in the brain. Annexin A5 can inhibit the over-activation of immune cells in the brain, thereby Annexin A5 can alleviate the nerve injury caused by the over-activation of immune cells in the brain and treat stroke.

According to embodiments of present disclosure, the cerebral stroke involves intracerebral nerve injury. Annexin A5 can play a neuroprotective role in the brain, repair nerve damage in the brain, and thus treat stroke.

According to embodiments of present disclosure, the cerebral stroke involves a damaged blood-brain barrier. Annexin A5 can repair the damaged blood-brain barrier and avoid further brain damage, thus treating stroke.

According to embodiments of present disclosure, wherein the immune cell comprises microglia. Over-activation of microglia can release a large number of neurotoxic factors, leading to neurodegenerative diseases. Annexin A5 can inhibit the over-activation of microglia.

According to embodiments of present disclosure, wherein the nerve injury is intracerebral nerve injury caused by oxygen/glucose deprivation. Annexin A5 can alleviate the intracerebral nerve injury caused by oxygen/sugar deprivation. Hypoxia or hypoglycemia in the brain can induce nerve injury. Annexin A5 can alleviate the nerve injury caused by oxygen and glycemia reduction and treat stroke.

According to embodiments of present disclosure, wherein the nerve injury is intracerebral nerve injury caused by excitotoxicity (excitatory toxicity). Excitatory toxicity can increase the content of calcium ions in brain tissues and activate NOS, which leads to a series of physiological or pathological changes such as the synthesis of large amounts of NO, resulting in nerve injury in brain. Annexin A5 can repair the nerve injury and treat stroke.

According to embodiments of present disclosure, wherein the nerve injury is intracerebral nerve injury caused by an endogenous substance.

According to embodiments of present disclosure, wherein the excitotoxicity is caused by N-methyl-D-aspartate.

According to embodiments of present disclosure, wherein the annexin A5 inhibits overactivation of immune cells in brain.

According to embodiments of present disclosure, wherein the annexin A5 repairs nerve injury in the brain.

According to embodiments of present disclosure, wherein the annexin A5 repairs the damaged blood-brain barrier.

According to embodiments of present disclosure, wherein the annexin A5 is nature human annexin A5. According to embodiments of present disclosure, wherein the annexin A5 or a functional equivalent thereof is a recombinant human annexin A5 expressed in a prokaryotic expression system. Therefore, recombinant human annexin A5 can be quickly and efficiently obtained by prokaryotic expression system, which is not expensive. Moreover, it has been proved that it has no immunotoxicity and very low immunogenicity. Moreover, the tolerant dose of A5 protein in rats and cynomolgus monkeys is above 4500 μg/kg, and even above 9000 μg/kg in rats. It is safe. Even in high dosage, it will not bring about the risk of drug use, this is of great therapeutic significance in treating cerebral stroke which is acute cerebrovascular disease. In some embodiments of the invention, the amino acid sequence of the annexin A5 expressed by the prokaryotic expression system is shown as SEQ ID NO:1. The amino acid sequence shown in SEQ ID NO:1 is identical with that of natural human annexin A5. The difference is that the N-terminal amino acid of the recombinant human annexin A5 is alanine (A), while the N-terminal amino acid of natural annexin A5 is acetylated alanine. It can be obtained efficiently and rapidly, and has been proved to be very safe, and will not cause risk of drug use even at high doses. It is of great value in the treatment of stroke.

According to embodiments of present disclosure, wherein the annexin A5 comprises an amino acid sequence of SEQ ID NO:1.

(SEQ ID NO: 1)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD

Moreover, it was found that the sequence of annexin A5 was conservative, and it had high homology in different species and played similar or identical roles. These highly homologous or conservative sequences of annexin A5 could be used to treat stroke or to prepare drugs for stroke. For example, in some embodiments of the invention, the sequence identity of the annexin A5 is more than 96% compared with natural human annexin A5, or with the sequence shown in SEQ ID NO:1, such as more than 96.5%, 97%, 97.5%, 98%, 98.3%, 98.5%, 98.8%, 99%, 99.3% and 99.5%. In some embodiments of the present invention, the annexin A5 comprise one conservative amino acid substitution, or two conservative amino acids substitution, or three conservative amino acids substitution, or four conservative amino acids substitution or five conservative amino acids substitution as compared with SEQ ID NO: 1. These highly homologous or conservative amino acid-substituted annexin A5 can be synthesized by artificial design, and can also be isolated or synthesized from natural annexin A5.

According to some embodiments of present disclosure, wherein the annexin A5 or the functional equivalent thereof is in a form of injection.

A5 protein can be used either single or multiple times. It can be administered by intravenous injection, intramuscular injection, intraperitoneal injection, subcutaneous injection, intrathecal injection, nasal spray and oral spray. It can also be short-term rapid medication, including, but not limited to, rapid intravenous injection, intramuscular injection, intraperitoneal injection, subcutaneous injection, intrathecal injection, nasal spray, oral spray, etc. It can be sustained exposure medication, including but not limited to sustained slow intravenous injection, intramuscular injection, intraperitoneal injection, subcutaneous injection, intrathecal injection, etc. Considering that A5 protein belongs to protein drugs, it is preferable to prepare injection by freeze-dried powder or other injection drugs with specific specifications, which can achieve rapid treatment and high bioavailability in vivo.

According to embodiments of present disclosure, wherein the annexin A5 or the functional equivalent thereof is administrated in a unit dosage form comprising 0.025 mg-250 mg the annexin A5 or the functional equivalent thereof.

According to embodiments of present disclosure, wherein the annexin A5 or the functional equivalent thereof is administrated in a unit dosage form comprising 1 mg-100 mg the annexin A5 or the functional equivalent thereof.

In some embodiments of the invention, the dosage of the annexin A5 is 0.05 mg-500 mg per day, preferably 2-200 mg. Usually it can be 1 mg-500 mg/day or 1 mg-450 mg/day, such as 1 mg-400 mg/day, 1 mg-350 mg/day, 1 mg-300 mg/day, 1 mg-250 mg/day, 1 mg-200 mg/day, etc. Of course, in some patients with mild stroke, the dosage of A5 protein can be less, such as 1 mg-100 mg/day, or 1 mg-80 mg/day.

Considering the daily dose of Annexin A5 of about 0.05 mg-500 mg, the content of Annexin A5 in unit dosage form can be adjusted to 0.025 mg-250 mg adaptively, such as 0.1-50 mg, 0.1-100 mg, 0.1-200 mg, or 0.1-250 mg, or 1-50 mg, 1-100 mg, 1-200 mg or 1-250 mg. Preferably, 1-100 mg. By preparing appropriate annexin A5 injection, the treatment of stroke can be achieved, and it is safe, non-toxic and having no side effects. Drugs in unit dosage form refer to a single dosage form that is designed when a drug is prepared into different dosage forms. For example, if a tablet is designed to be 400 mg in size, then 400 mg is a drug in a single dosage form. For example, drugs are designed as injections, and each injection is packaged independently as a single dosage form. Usually, a drug in a unit dosage form is used as a daily dose for one day or as a daily dose for half a day. The content of annexin A5 in these unit dosage forms can fluctuate between 0.025 and 250 mg, and then be prepared into unit dosage forms with other pharmaceutically available carriers.

These "pharmaceutically acceptable carriers" may include any and all solvents, dispersants, coatings, antibacterials and antifungal agents, isotonics and delayed absorbents that are physiologically compatible. Specific examples may be water, brine, phosphate buffer brine, glucose, glycerol, ethanol, and one or more of their compositions. In many cases, they can also be isotonic agents, such as carbohydrates, polyols (such as mannitol, sorbitol) or sodium chloride. Of course, pharmaceutically acceptable carriers can also include small amounts of auxiliary substances, such as wetting agents or emulsifiers, preservatives or buffers, to extend the shelf life or potency of antibodies.

During treatment, A5 protein can be used in acute and convalescent stage of stroke, secondary preventive administration after stroke, and preventive administration in potential stroke patients with imaging indications but without clinical symptoms.

Of course, A5 protein can be used alone in the treatment of stroke, or in combination with surgery or other drugs. Surgery includes but is not limited to endovascular interventional therapy (such as mechanical thrombectomy, angiogenesis and stent implantation). Other drugs include but are not limited to thrombolytic drugs (such as recombinant tissue plasminogen activator rtPA and urokinase), antiplatelet drugs (such as aspirin, clopidogrel, etc.), anticoagulants, defibrases (such as defibrase and batroxobin), and plasma expanders, drugs for vasodilators, other drugs for improving cerebral blood circulation and neuroprotective agents (e.g. edaravone, etc.). Through the combination of drugs, we can achieve multi-angle treatment of stroke, so that we can quickly treat stroke.

In some embodiments of the present invention, after administering an effective dose of annexin A5 to a subject, it can inhibit the over-activation of immune cells in the brain, such as the over-activation of microglia in the brain, thereby indirectly repairing the nerve injury caused by the over-activation of immune cells. At the same time, it can directly repair the brain nerve damage, such as reducing the brain nerve damage caused by oxygen/sugar deprivation, and reducing the brain nerve damage caused by excitotoxicity such as N-methyl-D-aspartate. In the process of treating stroke, on the one hand annexin A5 protein can penetrate into the brain through the damaged blood-brain barrier and play a therapeutic role. At the same time, it can repair damaged blood brain barrier to prevent further deterioration of the disease and further achieve the goal of treatment. In some embodiments of the invention, the annexin used is expressed by a prokaryotic expression system, such as an E. coli expression system, and the amino acid sequence of annexin A5 is shown in SEQ ID NO: 1.

In the second aspect of present disclosure, a pharmaceutical composition for treating cerebral stroke is provided, and according to embodiments of present disclosure, the pharmaceutical composition comprises an annexin A5 or a functional equivalent thereof.

In the third aspect of present disclosure, a drug combination is provided, and according to embodiments of present disclosure, the drug combination comprises (i) annexin A5 or a functional equivalent thereof; and (ii) an other drug for treating cerebral stroke other than (i).

According to embodiments of present disclosure, the other drug for treating cerebral stroke other than (i) comprises at least one selected from a group consisting of: a thrombolytic drug, an antiplatelet drug, an anticoagulant, an fibrinolytic drug, an plasma expander, an vasodilator or other drug to improve cerebral blood circulation and a neuroprotective agent. By using these drugs in combination, we can achieve multi-angle and multi-level treatment of stroke, so that we can quickly treat stroke.

DESCRIPTION OF DRAWINGS

The above and/or additional aspects and advantages of the present invention will become apparent and easy to understand from the description of the embodiments in conjunction with the following drawings, in which.

DETAILED DESCRIPTION OF THE INVENTION

Figure 1:
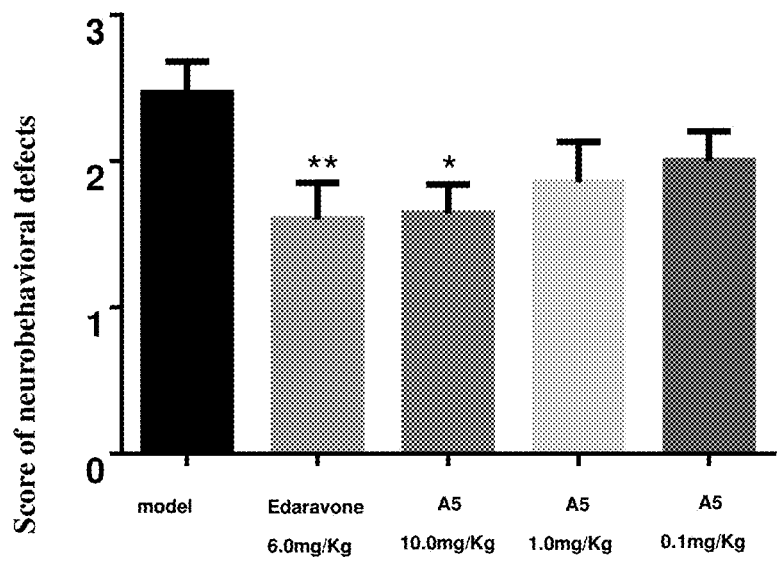
FIG. 1 is a result diagram of the effect of the annexin A5 solution on the symptoms of nerve defects.

The following embodiments described by reference to the accompanying drawings are illustrative and are intended to be used to explain the present invention rather than to constrain it.

Inventors of the present invention had found that annexin A5 can be used for treating stroke, repairing nerve injury of brain in a long-term study. It was confirmed by the rat model of ischemia-reperfusion that the annexin A5 could reduce the area of cerebral infarction, improve the symptoms of neurological deficits and promote long-term motor recovery in rats. For example, a rat model of focal cerebral ischemia was established by light irradiation, and then annexin A5 was injected into the caudal vein. The neurological deficit symptoms were improved and the area of cerebral infarction decreased significantly. Take another example, the rat model of hemorrhagic stroke was established by intracerebral injection of autologous arterial blood, and then the rats were injected with annexin A5 injection via caudal vein. The neurological deficit symptoms of the rats were significantly improved, and the area of cerebral infarction also decreased.

After a long period of research, the inventor found that annexin A5 can repair and alleviate stroke-related injuries, which can be used to treat stroke diseases. In this article, "repair" or "alleviate" refers to any way or means of reducing brain damage.

The annexin A5, which can repair or alleviate injury, or plays a role in stroke treatment, may be the full length or partial of amino acid sequence of the natural human annexin A5 polypeptide, or may be a variant of the full length or partial amino acid sequence of the natural human annexin A5 polypeptide. Of course, the preparation or acquisition of these natural annexins or variants can be based on any source or method, such as direct separation from naturally occurring substances, or direct artificial synthesization, or any combination of these methods.

For example, compared with human natural full-length annexin A5, available annexin A5 can have at least 97% sequence identity or 98% sequence identity, for example, at least 98.5%, at least 98.8%, or at least 99%, for example, at least 99.3% or at least 99.5%, or at least 99.6%. The amino acid sequences which are homologous to human natural full-length annexin A5 can have differences in one amino acid, two amino acids, three amino acids, four amino acids, or even five amino acids, six amino acids and seven amino acids. The amino acids differences can be conservative amino acids substitution in the natural full-length annexin A5 sequence. "Conservative amino acid substitution" can refer to the substitution of an amino acid by a biologically, chemically or structurally similar residue. Biological similarity refers to the biological activity of annexin A5 is not interrupted by the substitution. Structural similarity means that amino acids have side chains of similar length, such as alanine, glycine or serine, or side chains of similar size. Chemical similarity refers to that amino acids have the same charge or are all hydrophilic or all hydrophobic. For example, hydrophobic residues such as isoleucine, valine, leucine or methionine are substituted for each other. Or use polar amino acids such as arginine instead of lysine, glutamic acid instead of aspartic acid, glutamine instead of aspartic amide, serine instead of threonine and so on.

The above amino acid sequences, which show homology or conservative amino acid substitution, can be synthesized by artificial design and can also exist directly in other species in nature. It was found that the sequence of annexin A5 is conservative and show high homology in different species. The amino acid sequence of SEQ ID NO:1 is the same as that of natural human annexin A5, the difference is that the N-terminal amino acid of SEQ ID NO:1 is alanine (A), while the N-terminal of natural annexin A5 is acetylated alanine. Therefore, the mutated sites and amino acids in different species shown in Table 1 below are compared with SEQ ID NO:1 sequence, which also reflects the difference between the Annexin A5 sequences of different species in nature and the human natural Annexin A5 sequence. Compared with SEQ ID NO:1 sequence, the third amino acid mutated from valine to isoleucine in Gorilla gorillas. For another example, it is also reported in J. Mol. Biol. 223 (3), 683-704 (1992) and J. Mol. Biol. 223 (3), 683-704 (1992), there are variations in natural human annexin, that is, compared with natural annexin A5, the 76th amino acid mutates from glutamic acid to glutamine or from glutamic acid to glycine. Table 1 below lists the mutation sites and corresponding amino acids in some species compared with SEQ ID NO:1 sequence. These sequences can be obtained by NCBI Access Number in NCBI or directly in relevant references.

TABLE 1

Compared with SEQ ID NO: 1, the mutation sites and amino acids existed in different species

| Species | The corresponding loci in SEQ ID NO: 1 | Variation | NCBI Access Number or reference |
|---|---|---|---|
| Gorilla | 3 | V→I | XP_004040389.1 |
| human | 76 | E→Q | J. Mol. Biol. 223 (3), 683-704 (1992) |
| human | 76 | E→G | J. Mol. Biol. 223 (3), 683-704 (1992) |
| human | 134 | S→L | CAG38759.1 |
| Lipotes vexillifer | 53-54 | SA→AV | XP_007464903.1 |
|  | 207 | K→R |  |
| Orcinus orca | 53-54 | SA→AV | XP_004265141.1 |
|  | 207 | K→R |  |
|  | 318 | D→E |  |
| Tursiops truncatus | 53-54 | SA→AV | XP_004321032.1 |
|  | 207 | K→R |  |
|  | 272 | M→V |  |
| Lagenorhynchus obliquidens) | 53-54 | SA→AV | XP_026959424.1 |
|  | 207 | K→R |  |
|  | 272 | M→V |  |
|  | 88 | R→Q |  |
| Nomascus leucogenys | 141 | G→E | XP_003271381.1 |
|  | 209 | F→L |  |
|  | 317-318 | ED→GE |  |
| Delphinapterus leucas | 1-3 | AQV→SQA | XP_022451968.1 |
|  | 53-54 | SA→AV |  |
|  | 207 | K→R |  |
| Macaca fascicularis | 105 | N→D | NP_001270160.1 |
|  | 317-318 | ED→GE |  |
| Saimiri boliviensis | 54 | A→E | XP_010345019.1 |
|  | 51 | E→K |  |
|  | 315 | C→CG |  |

The scheme of the present invention will be explained with embodiments. It will be understood by those skilled in the art that the following embodiments are used only to illustrate the present invention and should not be regarded as limiting the scope of the present invention. If no specific technology or condition is specified in the embodiments, it shall be carried out in accordance with the technology or condition described in the literature in the field or in accordance with the product specification. The reagent or instrument used does not specify the manufacturer, and is a conventional product that can be purchased from the market.

EXAMPLE 1

A5 protein comes from human full-length annexin. By constructing recombinant vector, A5 protein was expressed in E. coli. After sequencing, the amino acid sequence of A5 protein was as follows:

(SEQ ID NO: 1)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD.

As shown in SEQ ID NO:1, annexin A5, expressed by E. coli expression system, contains 319 amino acids. The cDNA sequence is encoded by 320 amino acid codons, and methionine at N-terminal is removed during expression. The amino acid sequence of SEQ ID NO:1 is identical to that of natural human annexin A5, except that the N-terminal amino acid of recombinant human annexin A5 expressed by this system is alanine (A), while the N-terminal amino acid of natural human annexin A5 is acetylated alanine.

The annexin A5 obtained from example 1 is then used to perform the following experiments:

EXAMPLE 2

Refer to the literature Behavioral deficits and recovery following transient focal cerebral ischemia in rats: glutamatergic and GABAergic receptor densities (Jolkkonen J, Gallagher N P, Zilles K, Sivenius J. Behav Brain Res 2003; 138:187-200) and literature Reversible middle cerebral artery occlusion without craniectomy in rats. (Longa E Z, Weinstein P R, Carlson S, Cummins R. Stroke 1989; 20:84-91), the cerebral ischemia-reperfusion model of middle cerebral artery occlusion (MCAO) was established by internal carotid artery thread embolization. The A5 (annexin A5) group was 0.1 mg/kg, A5 1.0 mg/kg and A5 10.0 mg/kg, respectively. Edaravone was injected intravenously (6.0 mg/kg) as the positive control group. The model group and sham operation group were set up separately. The model group and sham operation group were given 0.9% sodium chloride injection of the same volume. Each dose group of A5 injection can be given once at the time of reperfusion, once again at 1 hour after reperfusion, and the other groups can be given once immediately after reperfusion. After 24 hours of cerebral ischemia, the symptoms of neurobehavioral deficits and the area of cerebral infarction were evaluated.

1 Experimental Materials (1) Experimental Animal

Sprague Dawley (SD) rat, SPF grade, male, aged 6-8 weeks or so, weighing 250-280 g.

Animals will be excluded in the course of the experiment in situations as follows: a) death during anesthesia; b) death during cerebral ischemia; c) death after reperfusion until the evaluation of the index; d) detection of basilar hemorrhage after brain extraction; e) right cerebral infarction-free area after TTC staining.

(2) reagents

The solution of annexin A5 is prepared by diluting the A5 protein prepared in example 1 with 0.9% sodium chloride injection.

Control substance: Edaravone Injection (purchased from Nanjing Xiansheng Dongyuan Pharmaceutical Co., Ltd.) was diluted with 0.9% sodium chloride injection in the proportion of 1:1 as a positive control.

2 Experimental Design (1) Dose Design

TABLE 2

Dose Table for Pharmacodynamic Test of A5 Injection

| Group | Test | Dosage (mg/kg) | Preparation concentration (mg/mL) | Dosage volume (mL/kg) | Number of main test animals |
|---|---|---|---|---|---|
| A5 0.1 mg/kg group | A5 injection | 0.1 | 0.02 | 5 | ~20 |
| A5 1.0 mg/kg group | A5 injection | 1.0 | 0.2 | 5 | ~20 |
| A5 10.0 mg/kg group | A5 injection | 10.0 | 2 | 5 | ~20 |
| Edaravone | Edaravone injection | 6.0 | 1.0 | 6 | ~20 |
| model group | 0.9% sodium chloride injection | — | — | 5 | ~20 |
| sham operation group | 0.9% sodium chloride injection | — | — | 5 | ~10 |

(2) Drug Administration

The animals in each group were injected intravenously through the caudal vein at a rate of about 1.5-2.5 ml/min.

After 24 hours of cerebral ischemia, the symptoms of neurobehavioral defects and the area of cerebral infarction were evaluated.

3 Evaluation Method (1) Neurological Deficit Symptom Score

According to the method described in Rat middle cerebral artery occlusion, evaluation of the model and development of a neurologic examination (Bederson J B, Pitts L H, Tsuji M, Nishimura M C, Davis R L, Bartkowski H. 1986. Stroke 17: 472-476), the neurological deficit symptoms of animals were evaluated by the improved Bederson 5-point system after 24 hours of ischemia.

(2) Measurement of the Degree of Cerebral Infarction

According to Evaluation of 2,3,5-triphenyltetrazolium chloride as a stain for detection and quantification of experimental cerebral infarction in rats (Bederson J B, Pitts L H, Germano S M, Nishimura M C, Davis R L, Bartkowski H M. Stroke 1986; 17: 1304-8) and Quantification of infarct size on focal cerebral ischemia model of rats using a simple and economical method (Yang Y, Shuaib A, Li Q. J Neurosci Methods 1998; 84:9-16), determine the degree of cerebral infarction by TTC staining.

Calculation of infarct area: the photos were processed by Image J software, and the corresponding area of left brain and non infarct area of right brain were calculated according to the formula, and the percentage of infarct area was calculated.

Method of Infarct volume calculation:

$$V = t(A1 + A2 + A3 + \ldots + An)$$

t is the slice thickness, A is the infarct area.

$$\% I = (V_C - V_L)/V_C \times 100\%$$

% I is the percentage of infarct area, $V_C$ is the volume of control side (left hemisphere), $V_L$ is the volume of non infarct area of infarct side (right hemisphere).

(3) Evaluation Index

The range of cerebral infarction and neurobehavioral score were used as the main evaluation indexes, and the clinical manifestations of animals were observed.

The quantitative data were expressed as mean±standard error. Each efficacy index was analyzed by one-way ANOVA with Graphpad prism (6.01). After significant variance test, Fisher's LSD test was used to test the differences between groups. P<0.05 was defined as significant difference.

4 Experimental Results (1) The Effect of A5 Injection on the Symptoms of Nerve Deficiency With one-way analysis of variance, there was no statistical difference between the groups (f (4.69)=2.305, P=0.0669). However, t-test was carried out between each group and model group respectively. Edaravone 6.0 mg/kg group (P<0.01) and A5 10.0 mg/kg group (P<0.05) could significantly improve the neurobehavioral deficit symptoms of ischemic animals; A5 1.0 mg/kg group and A5 0.1 mg/kg group had the tendency to improve the neurobehavioral deficit symptoms of ischemic animals, but there was no statistical difference. The influence of A5 injection on neurobehavioral defects is showed in Table 3 and FIG. 1.

TABLE 3

The effect of A5 injection on acute cerebral ischemia-reperfusion injury in rats (Mean ± SEM)

| Group | The number of rats | Neurological deficit symptom score | Scope of cerebral infarction (%) |
|---|---|---|---|
| sham operation group | 10 | 0 | 0 |
| model group | 15 | 2.47 ± 0.22 | 42.53 ± 3.27 |
| Edaravone 6.0 mg/kg | 15 | 1.60 ± 0.25** | 35.93 ± 3.94 |
| A5 10.0 mg/kg | 14 | 1.64 ± 0.20* | 28.97 ± 5.08# |
| A5 1.0 mg/kg | 14 | 1.86 ± 0.27 | 38.37 ± 3.61 |
| A5 0.1 mg/kg | 16 | 2.00 ± 0.20 | 43.61 ± 3.60 |

Compared with the model group,
*P < 0.05,
**P < 0.01,
P < 0.05

(2) Effect of A5 Injection on the Scope of Cerebral Infarction

Figure 2:
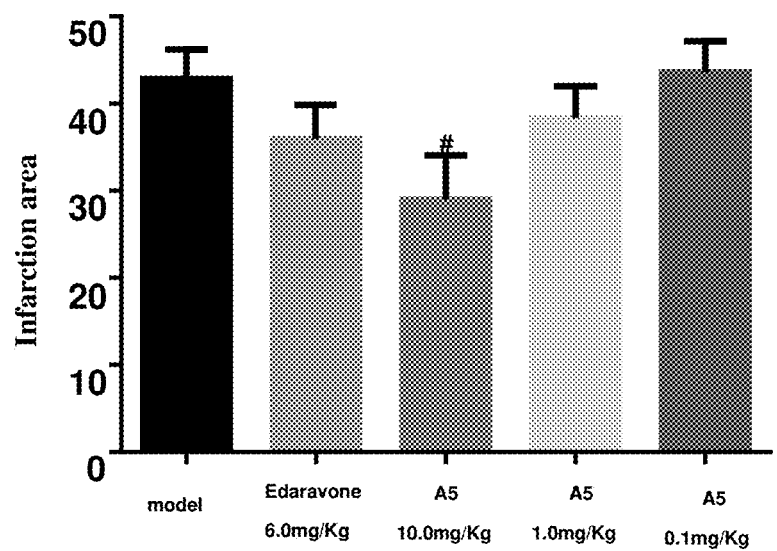
FIG. 2 is a result diagram of the effect of annexin A5 solution on the scope of cerebral infarction.

With one-way analysis of variance, there was no statistical difference between the groups ($F_{(4,69)}$=2.240, P=0.0735). However, t-test was carried out between each group and the model group respectively. A5 10.0 mg/kg group (P<0.05) could significantly reduce the cerebral infarct area of model animals; edaravone 6.0 mg/kg group and A5 1.0 mg/kg group had the trend of reducing the cerebral infarct area of model animals, but there was no statistical difference; A5 0.1 mg/kg group had no effect on reducing the cerebral infarct area of model animals. The influence of A5 injection on the area of cerebral infarction is shown in Table 3 and FIG. 2.

In this experiment, the difference in the scope of cerebral infarction in the model group was basically within 1/3 of the average (mean±SD, 42.53±12.65), and the model availability rate was 69.81% (excluding the sham operated group); the experimental system was reliable and could be used for efficacy evaluation.

Compared with the model group, A5 10.0 mg/kg group can significantly reduce the cerebral infarction area of the model rats (P<0.05); edaravone 6.0 mg/kg, A5 1.0 mg/kg group has the trend of reducing the cerebral infarction area of the model rats, but there is no statistical difference; A5 0.1 mg/kg has no effect on reducing the cerebral infarction area of the model rats. Compared with the model group, edaravone 6.0 mg/kg and A5 10.0 mg/kg can significantly improve the neurobehavioral deficit symptoms of ischemic animals (P<0.01, P<0.05); the other groups do not show significant improvement in this index.

In this experiment, A5 10.0 mg/kg group can significantly reduce the area of cerebral infarction in rats with ischemia, and improve the symptoms of neurobehavioral defects in rats with ischemia. There was no bleeding risk in the experimental group treated with annexin A5.

EXAMPLE 3

Microglia plays an important role in the inflammatory process of the central nervous system. The moderate activation of microglia can protect neurons, but the over activated microglia will release a large number of neurotoxic factors, such as carbon monoxide, which will lead to the occurrence of neurodegenerative diseases. Lipopolysaccharide (LPS) can activate microglia, which leads to the over activation of microglia and the damage of neurons. A5 was used to observe the effect of LPS on the over activation of microglia.

During the experiment, LPS was used to stimulate the primary purified microglia as the control group, and A5 protein was added as the experimental group. For the above treatment, MTT method was used to detect cell viability, and cellular immunochemistry method was used to observe cell morphological changes. The results showed that LPS could activate the primary microglia, but not the cell viability. A5 protein can inhibit the over activation of microglia induced by LPS. Therefore, A5 protein can be used to inhibit the over activation of immune cells in the brain, such as microglia.

EXAMPLE 4

Oxygen glucose deprivation (OGD) model is a stimulation model simulating ischemia/hypoxia at the cell level. By changing the cell culture conditions, such as putting the cells into the hypoxia box or into the sugar free medium, the damage of cells under the condition of ischemia/hypoxia is simulated.

OGD model was established with primary cortical neurons. The cells in the culture plate were washed twice with PBS, and then the glucose-free DMEM exchanged with 95% $N_2$+5% $CO_2$ for 30 minutes was added. Then the cells were quickly placed in 37° C., 94% $N_2$+1% $O_2$+5% $CO_2$ hypoxia incubator. After 8 hours of anoxic culture, the corresponding DMEM medium (i.e. DMEM medium containing A5) was added, and then put the plate into a 37° C. 5% $CO_2$ cell incubator for 24 hours of reoxygenation. After 24 hours of culture, morphological changes were observed under inverted microscope, cell survival rate was detected by CCK-8 colorimetry and apoptosis rate was detected by flow cytometry. At the same time, the treatment group of normoxia and normal glucose was set as the control group.

The experimental results showed that A5 treatment group could reduce the damage of neurons caused by oxygen glucose deprivation.

EXAMPLE 5

Example 5 studied the neuroprotective effect of A5 protein on NMDA (N-methyl-D-aspartate)—induced excitotoxic damage on cortical neurons in rats. NMDA can activate NMDA receptor to increase $Ca^{2+}$ content in brain tissue, and NOS is activated in a large amount, which leads to a series of physiological or pathological changes such as the synthesis of a large number of NO, causing damage to neurons in brain. In order to observe the neuroprotective effect of A5 protein on neuronal damage induced by excitotoxicity, the neuron was pretreated with A5 protein.

In the experiment, 17 day embryonic SD rats were selected and the cortical neurons were cultured. Then the neurons were divided into control group, NMDA group and A5 pretreatment group. The neurons in NMDA group were added with NMDA for exposure, and the neurons in A5 pretreatment group were incubated with A5 protein for a period of time, and then added with NMDA. For different treatment groups, trypan blue staining was used to evaluate cell viability, TUNEL staining was used to detect apoptosis cells and immunofluorescence cytochemistry was used to detect neuron morphology.

The results showed that compared with NMDA group, A5 pretreatment group could reduce the damage of excitatory toxicity to neurons.

EXAMPLE 6

Blood brain barrier is composed of three components: brain microvascular endothelial cells, astrocytes and basement membrane. The damage of blood-brain barrier is one of the important pathology of stroke.

In the experiment, the blood-brain barrier model was established by co-culturing spontaneously transformed endothelial cell line and purified rat astrocytes. The blood-brain barrier (BBB) model in vitro was injured after stimulation, and then treated with A5 protein. The experimental results show that after stimulation, the established blood-brain barrier will be significantly damaged, and A5 can repair the damaged blood-brain barrier.

EXAMPLE 7

Immunotoxicity and Immunogenicity Study
(Repeated Dose Toxicity Study with SD Rats and Cynomolgus Monkeys)

1. Toxicity Study with SD Rats

SD rats were given A5 protein intravenously for 28 days, and a recovery period of 4 weeks was set up to observe the toxic reaction and severity, main toxic target organs and reversible degree of damage. The dosage was 0 (blank adjuvant), 30, 150 and 750 µg/kg respectively. Blood was sampled to detect immunotoxicity ($CD4^+$, $CD8^+$ T cells) and immunogenicity. The experiment was divided into four groups, and there were eight rats in each group. The samples were collected at four time points, that is, each rat was sampled for serum at four time points.

The results of immunotoxicity showed that compared with control group, there was no significant difference in the proportion and ratio of peripheral blood T-lymphocyte subsets (CD4$^+$, CD8$^+$ T cell test values) of each dose group.

The immunogenicity results are shown in Table 4. The number of samples in each group in Table 4 represents 8 rats in each group, and each rat is sampled at four time points, with a total of 32 samples in each group; the number of positive sample is the number of positive samples detected in each group.

TABLE 4

Anti-drug antibody data of A5 protein in rat serum

| | Group | | | |
|---|---|---|---|---|
| | Control group | 30 μg/kg dose group | 150 μg/kg dose group | 750 μg/kg dose group |
| Dosage | 0 μg/kg | 30 μg/kg | 150 μg/kg | 750 μg/kg |
| Number of samples in each group | 32 | 32 | 32 | 32 |
| Number of positive samples | 0 | 21 | 22 | 20 |
| Positive rate of total samples | 0.0% | | 65.6% | |

It can be seen from the results given in Table 4 that no anti-drug antibody (ADA) was detected in SD rats after intravenous administration of A5 protein blank adjuvant. After intravenous injection of different doses of A5 protein, the positive rate was 65.6%. There was no significant difference among the dose groups. The positive samples were mainly occurred after the last administration and at the end of the recovery period, which was consistent with the process of the production of drug-resistant antibodies in vivo.

2. Toxicity Study with Cynomolgus Monkeys

In this study, A5 protein was injected intravenously into cynomolgus monkeys for 28 days, and a recovery period of 4 weeks was set up to observe the toxic reaction and severity, the main toxic target organs and the reversible degree of damage in cynomolgus monkeys. The dosage was 0 (blank adjuvant), 15, 75 and 375 m/kg respectively. Blood was sampled to detect immunogenicity and immunotoxicity (CD4$^+$, CD8$^+$ T cells).

The results of immunotoxicity showed that compared with control group, there was no significant difference in the proportion and ratio of peripheral blood T-lymphocyte subsets (CD4$^+$, CD8$^+$ T-cell measured value) of each dose group.

The immunogenicity results are shown in Table 5. Using the same grouping and processing method as the rats in foregoing paragraphs, the difference is that when sampling, there are two more samples in each group.

TABLE 5

Data of anti-drug antibody to A5 protein in monkey serum

| | Groups | | | |
|---|---|---|---|---|
| | Control | 15 μm/kg dose group | 75 μg/kg dose group | 375 μm/kg dose group |
| Dosage | 0 μg/kg | 15 μg/kg | 75 μg/kg | 375 μg/kg |
| Number of samples in each group | 34 | 34 | 34 | 34 |
| Number of positive samples | 0 | 7 | 6 | 13 |
| Positive rate of total samples | 0.0% | | 25.5% | |

It is not difficult to see from the results given in Table 5 that ADA was not detected in cynomolgus monkeys after intravenous administration of A5 protein blank adjuvant. After intravenous injection of different doses of A5 protein injection, the detection rate of the positive samples was 25.5%. The positive samples mainly occurred after 4 weeks of administration and at the end of the recovery period, which was consistent with the process of the production of drug-resistant antibodies in vivo.

The results showed that no immunotoxicity was found in rats and cynomolgus monkeys. In the immunogenicity test, the positive rate of cynomolgus monkeys was significantly lower than that of rats. Considering that A5 protein belongs to human protein, it is expected that its immunogenicity incidence in human body will be significantly reduced.

EXAMPLE 8

Study on Toxicity of A5 Protein in Single Intravenous Injection in SD Rats and Cynomolgus Monkeys 1. Toxicity of A5 Protein in Single Intravenous Injection in SD Rats In this study, A5 protein was injected intravenously once in SD rats to observe the acute toxicity, severity and main toxic target organs. The dosage was 0 (blank adjuvant), 1000, 3000 and 9000 μg/kg respectively. After the intravenous injection, the animal's posture, gait, reaction, nerve activity, appetite, fur, eyes, ears, mouth, nose, limbs, breath, feces and other clinical symptoms were observed continuously. After that, the recovery from toxic reaction was observed continuously until the 14th day after administration. The animals were dissected and examined for macropathology 15 days after administration. During the experiment, the clinical symptoms of all animals were normal; the weight changes of female and male animals in the administration group were normal; no abnormality was found in all tissues and organs in the macropathological examination. The maximum-tolerated dose (MTD) of single intravenous injection of A5 protein was more than 9000 m/kg.

2. Toxicity of A5 Protein in Single Intravenous Injection in Cynomolgus Monkeys

A single intravenous injection of A5 protein was used to observe the acute toxicity and its severity and main toxic target organs in cynomolgus monkeys. The dosage was 0 (blank adjuvant), 500, 1500 and 4500 μg/kg respectively. After the single intravenous injection, observe the clinical symptoms of the animals (including feces, appearance, respiration, nerve reaction, activity status, etc.) until the 15th day after the administration. After administration, the food intake was measured once a day and the body weight was measured once a week. The body temperature, blood pressure and electrocardiograph (ECG) of the animals were measured before and after administration on the day of administration, and again on the 1st, 7th and 15th day of administration. Hematology (including blood coagulation) and serum biochemical examination were carried out for all animals on the 1st, 7th and 15th day after administration, and urine examination was carried out on the 14th day after administration. On the 15th day after administration, the animals were dissected for macropathological examination, and if necessary, for histopathological examination. Results showed that there were no significant changes in clinical symptoms, injection site, body weight, food intake, body temperature, blood pressure, ECG, urinalysis, serum biochemical and pathological examination. There was no significant change in prothrombin time (PT), activated partial thromboplastin time (APTT) and thrombin time (TT) on the 13th day of quarantine period, the 1st day and the 15th day after administration. In this experiment, the maximum-tolerated dose (MTD) of cynomolgus monkeys was more than 4500 m/kg.

The above results showed that the tolerance dose of A5 protein was more than 4500 μg/kg in both SD rats and cynomolgus monkeys, and even more than 9000 μg/kg in SD rats. The results showed that there was no significant toxicity of A5 protein in rats and monkeys. Therefore, we are reminded that A5 protein is safe for the treatment of stroke, and even in the case of high dosage, it will not or almost will not bring the risk of medication.

In the description of the specification, the terms "one embodiment", "some embodiments", "examples", "specific examples", or "some examples" means that the specific features, structures, materials or features described in combination with the embodiment or examples are included in at least one embodiment or example of the invention. In this specification, the schematic expression of the above terms need not be directed to the same embodiment or example. Moreover, the specific features, structures, materials or features described may be combined in an appropriate manner in any one or more embodiments or examples. In addition, without contradiction, those skilled in the art can combine and combine different embodiments or examples described in the specification and features of different embodiments or examples.

Although the embodiments of the invention have been shown and described above, it can be understood that the above embodiments are exemplary and cannot be understood as limitations of the invention. Ordinary technicians in the art can change, modify, replace and transform the above embodiments within the scope of the invention.

What is claimed is:

1. A method for repairing a damaged blood-brain barrier in a patient, the method comprising: administrating to the patient in need thereof an effective dose of an annexin A5 having the amino acid sequence of SEQ ID NO:1, wherein the annexin A5 penetrates into the brain through the damaged blood-brain barrier and plays a therapeutic role and wherein the annexin A5 repairs the damaged blood-brain barrier to prevent further deterioration of damage to the blood-brain barrier.

2. The method of claim 1, wherein the annexin A5 is a recombinant human annexin A5 expressed in a prokaryotic expression system.

3. The method of claim 1, wherein the annexin A5 is in a form of injection.

4. The method of claim 1, wherein the annexin A5 is administrated in a unit dosage form of 0.025 mg-250 mg.

5. The method of claim 4, wherein the annexin A5 is administrated in a unit dosage form of 1 mg-100 mg.

6. The method of claim 1, wherein the method does not result in an increased risk of bleeding.

* * * * *